United States Patent [19]

Burr et al.

[11] 4,404,840
[45] Sep. 20, 1983

[54] DEVICE FOR EVALUATING ABRASIVE WEAR OF ELASTOMERIC O-RING MATERIALS

[76] Inventors: Bruce H. Burr, 10203 Sagedown La., Houston, Tex. 77089; Kurt M. Marshek, 9701 Courtleigh Cir., Austin, Tex. 78759

[21] Appl. No.: 264,687

[22] Filed: May 18, 1981

[51] Int. Cl.$^3$ ............................................. G01N 3/56
[52] U.S. Cl. ............................................. 73/7; 73/766
[58] Field of Search ........................................ 73/7, 9

[56] References Cited

U.S. PATENT DOCUMENTS

| | | | |
|---|---|---|---|
| 1,444,803 | 2/1923 | Ratner et al. | 73/7 |
| 2,808,719 | 10/1957 | Kommers | 73/7 |
| 2,970,411 | 2/1961 | Trolander | 73/7 X |
| 3,592,362 | 7/1971 | Kane | 73/7 |
| 3,717,025 | 2/1973 | Kronenberg | 73/9 |

OTHER PUBLICATIONS

Publ.—"O-Ring Wear Test Machine" by B. H. Burr et al., pp. 1–12, Wear vol. 68, No. 1, (pp. 21–32).
Publ.—"Friction and Wear Characteristics of Plastic Guides", D. K. Pal et al., J. Inst. Eng., (India), vol. 50, No. 11, 7/1970, (pp. 298–306).

*Primary Examiner*—Daniel M. Yasich

[57] ABSTRACT

An abrasive wear tester wherein a segment of a relatively small diameter O-ring is held in contact with a rotating cylindrical disk. The disk is mounted to rotate about its longitudinal axes at a known rate for a specified period of time. The O-ring segment and cylinder are immersed in an abrasive fluid. The abrasive particles are pulled between the wear surfaces causing removal of the surface materials, predominantly the softer O-ring material. The O-ring specimen is cut from an O-ring and weighed prior to test. After the test the O-ring segment is again weighed and the weight of material removed by wear is calculated. These measurements indicate the wear resistance of the O-ring being tested. Service loads or pressures are simulated by means of a cable and weight system urging the O-ring against the cylindrical wear disk surface by means of a lever arm pulley arrangement or similar loading device.

8 Claims, 3 Drawing Figures

DEVICE FOR EVALUATING ABRASIVE WEAR OF ELASTOMERIC O-RING MATERIALS

Invention described herein may be manufactured, used, and sold by the Hughes Tool Company on a royalty free basis.

BACKGROUND OF THE INVENTION

The present invention relates generally to the field of wear and friction measuring or testing and in particular to a method and apparatus for measuring the dynamic coefficient of friction and the wear of an elastomeric O-ring material, circular wire, tubing and the like. The method and apparatus also find use in measuring or testing the effect of lubricants on wear as well as the mating O-ring surface. Friction wear measuring devices are known to the prior art. They generally operate by developing linear forces between the surface under test and a mating surface. The force necessary to move the counter face surface relative to the test surface is utilized to determine the coefficient of friction. The wear is generally measured by determining either the volume or the weight of the specimen before the test begins and subtracting the volume or the weight of the specimen after completion of the test.

While these devices are to some extent useful in developing information about the wear of specimens of material, they are substantially useless in so far as determining wear and coefficients of friction of actual O-rings. Furthermore, the present device utilizes standard size O-rings which can be bought from O-ring manufactures. Segments are cut from this standard O-ring and hence do not require special molding or cutting from bulk materials. The present invention is directed to an advanced method and apparatus for measuring and testing dynamic coefficients of friction and abrasive wear rates of elastomeric O-rings, which overcome each of the disadvantages and draw backs of known prior art techniques.

SUMMARY OF THE INVENTION

The present invention relates to a wear and friction measuring and testing apparatus which is easily fabricated from standard machine components and capable of accurately measuring wear rates, dynamic coefficients of friction and relative wear rates between various O-ring material. The present invention also relates to a method for measuring and testing wear rates and dynamic coefficients of friction.

In a specific embodiment, the inventive device comprises a wear cylinder with a rotatable mounting shaft which is held by a drill press chuck or other coupling. On each side of the wear cylinder, a vertical loading arm is mounted on a ball bearing supported shaft. At the bottom of the loading arm is the specimen holder. This holder holds the O-ring segment against the wear cylinder. The top of the loading arm is connected to a dead weight by means of a steel cable wrapped over a pulley. The dead weight is located under the table which supports the loading arm mechanism. The test specimens and wear cylinder are immersed in a container of test fluid which may be heated to provide data for elevated temperatures. A friction force exerted on the O-ring specimen by the wear cylinder is measured by means of strain gauges mounted on each vertical loading arm. Two gauges are mounted on one side of the loading arm, and two gauges are mounted on the opposite side. The two gauges on each side of the loading arm are mounted in a mutually perpendicular manner, with one being aligned along the longitudinal loading arm axes. This arrangement provides for complete temperature compensation and increased output. A conditioning unit is used to balance the circuit, provide the DC input, and amplify the output of the strain gauge bridge. The output signal from the conditioning unit is plotted by a recorder. The friction force measuring set up is calibrated by hanging a dead weight from the specimen holder. After removing the dead weight, a resistance necessary to cause full scale deflection on the recorder is placed across one leg of the bridge. This resistance substitution box is then used for frequent calibration checks throughout the test program. The dead weight calibration is performed when the machine is dissembled and the loading arms are positioned horizontally.

The temperature of the O-ring specimen is monitored using a microminiature thermocouple. This thermocouple is inserted in a small diameter hole drilled in the specimen. The thermocouples are connected to conditioning units that amplify the outputs. The outputs are plotted by a chart recorder directly in degrees Fahrenheit above room temperature.

It is accordingly one object of the present invention to provide an improved method and apparatus for measuring and comparing the relative wear resistance of O-rings.

A further object of the present invention is to provide a friction measuring apparatus and testing method capable of determining dynamic coefficients of friction characteristics. Another object of the present investigation is to provide an apparatus for measuring O-ring specimen temperatures during wear tests.

Still a further object of the present invention is to provide an apparatus which reproduces the wear surfaces found on O-rings in actual service. Still a further object of the present invention is to provide a means of evaluating the influence of various fluid environments on wear. Yet another object of the present invention is to provide a method and apparatus for testing two or more O-rings simultaneously under the same or different loading conditions. These and other objects of the present invention, as well as many of the attendant advantages thereof, will become more readily apparent when reference is made to the following description, taken in accordance with the accompanying drawings.

DETAILED DESCRIPTION OF THE DRAWINGS

Figure 1:
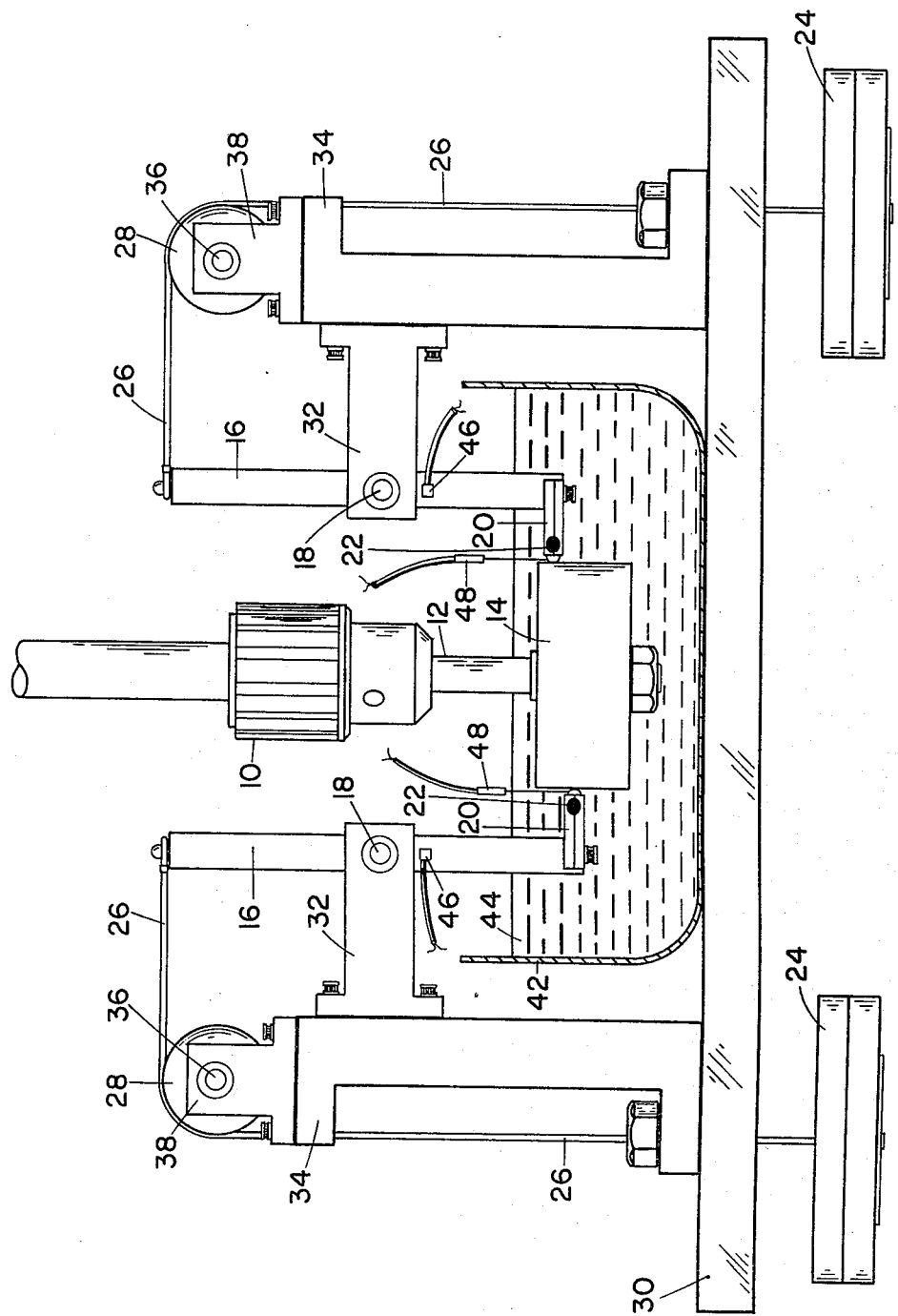
FIG. 1 is a front view, partially in section, of the inventive measuring and testing device.

With reference to FIG. 1, the mechanical configuration of the inventive device for measuring and testing will be described. The inventive measuring and testing device comprises a standard chuck or coupling means 10 which holds the mounting shaft 12 of the wear cylinder 14, the mounting shaft 12 being rotatably driven by means (not shown). On each side of the wear cylinder 14, a vertical loading arm 16 is mounted on a ball bearing supported shaft 18. At the bottom of the loading arm 16 is the specimen holder assembly 20. An O-ring segment 22 is held by the holder assembly 20. The top of the holding arm 16 is connected to a dead weight 24 by means of a steel cable 26 wrapped over a pulley 28. The dead weight 24 is located under the table top 30. The shaft hanger 32 which supports bearing 18 is attached to channeled bracket 34. Pulley 28 is supported by ball bearing supported shaft 36. The shaft 36 is supported by shaft hanger 38 which is mounted on channel bracket 34. Channel bracket 34 is bolted to table top 30.

The lengths of the two loading arms 16 are different so the O-ring specimens 22 would not ride on the same cylinder 14 wear track. The dead weights 24 for each loading arm 16 were designed based on the respective loading arm length so that precise loading forces could be obtained.

A hole, centered under the wear cylinder 14, is cut in the table top 30 so that a container 42 of test fluid 44 of water, and/or thickeners could be raised to submerge the test specimens 22 and wear cylinder 14. The fluid container 42 is supported by a recessed hole cover plate which sets in table top 30.

Strain gauges 46 are mounted on each vertical loading arm 16. On each loading arm 16 four strain gauges 46 are mounted immediately below the support shaft 18 near the point of maximum bending moment. Two gauges 46 are mounted on one side of the loading arm 16, and two gauges 46 are mounted on the opposite side. The four gauges form the four legs of a Wheatstone Bridge. The two gauges 46 on each side of the loading arm 16 are mounted in a mutually perpendicular manner, with one being aligned along the longitudinal loading arm axes. This arrangement provides for complete temperature compensation and increased output. The output of all gauges are additive providing an increased strain sensitivity.

The temperature of the O-ring specimens 22 is monitored using a microminiature syringe type thermocouple 48. These thermocouples are inserted in small diameter holes drilled in the specimens 22. The thermocouples are connected to conditioning units that amplify the outputs. The outputs are plotted by a strip chart recorder directly in degrees Faharenheit above room temperature.

Figures 2, 3:
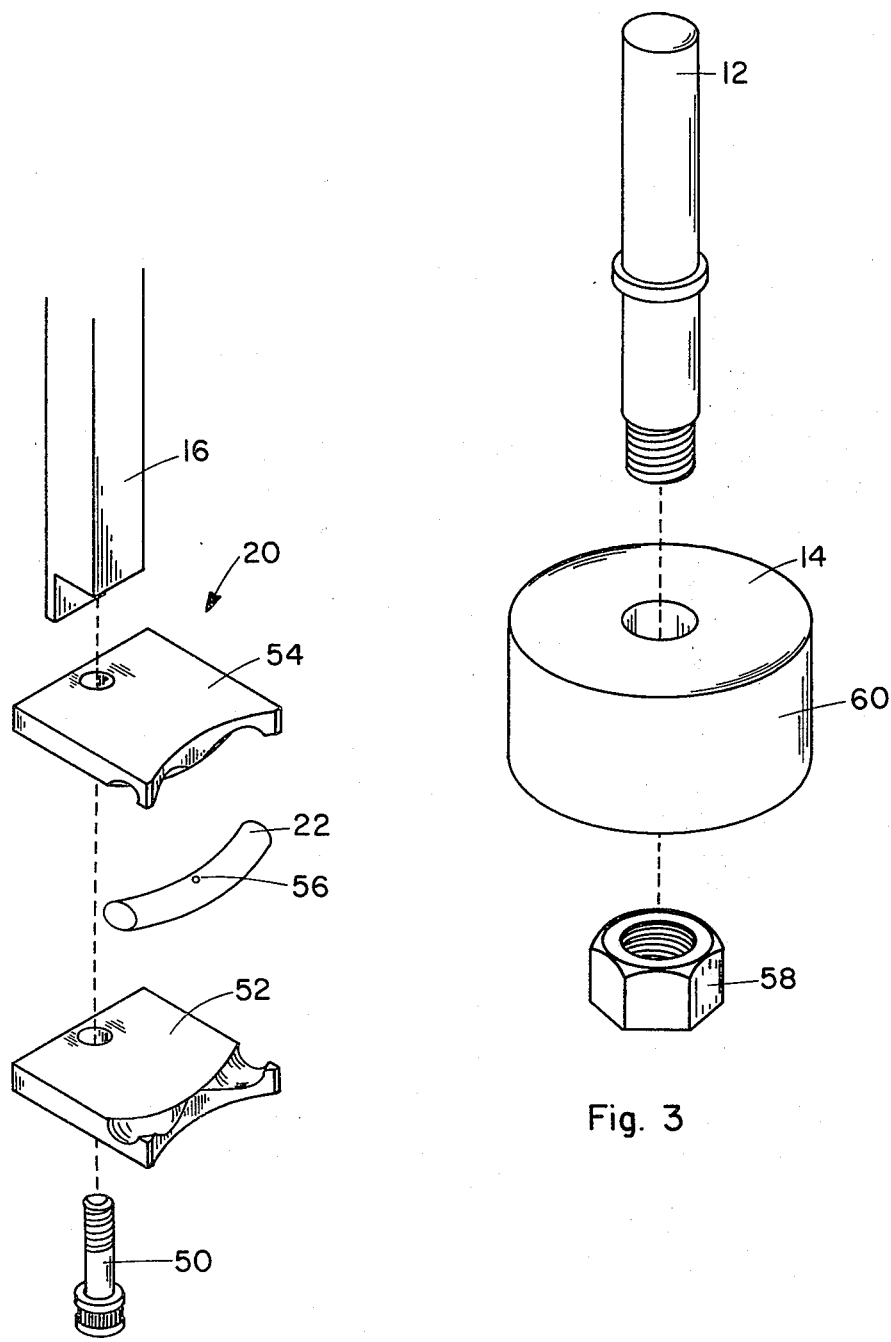
FIG. 2 is an exploded view of the specimen holder and lower portion of the loading arm used in the inventive device.
FIG. 3 is an exploded view of the wear cylinder and mounting shaft used in the inventive device.

FIG. 2 illustrates specimen holder assembly 20. Bolts 50 clamp specimen 22 which has drilled hole 56 between lower specimen holder plate 52 and upper specimen holder plate 54 to bottom of loading arm 16. The bottom recess portion of loading arm 16 prevents rotation of holder assembly 20.

FIG. 3 illustrates assembly of the wear cylinder 14 to the mounting shaft 12 with nut 58. Nut 58 is tightened to prevent rotation of wear cylinder 14 on mounting shaft 12.

Wear cylinder 14 has a sand-blasted surface 60 which is necessary to cause a measurable amount of specimen wear in a short time. The lightly sand blasted wear cylinder surface 60 creates a roughness that tends to draw abrasive particles from the test fluid environment into the interface between the O-ring specimen 22 and the wear cylinder surface 60. This action causes three body abrasive wear.

OPERATION

The operation or experimental procedure of the invention is summarized as follows:

The specimens 22 are cut from a standard size O-ring. Using the specimen holder assembly 20 as a die, the O-ring segment 22 is trimmed with a razor blade to exactly fit the specimen holder assembly 20. Five specimens are cut from one O-ring with little waste.

A special hole 56 is drilled at the center O-ring specimen 22 as shown in FIG. 2. The specimens 22 are measured and marks are placed where the holes 56 are to be drilled. Using the specimen holder 20 to restrain the specimen 22 and keep it perpendicular to the drill bit, a small hole is drilled. The drilling depth is set to one-half the cross section diameter of the O-ring specimen 22. Special holes are drilled for thermocouple probes 48 which are installed to monitor temperature.

Each specimen 22 is weighed on an analytical balance to the nearest ten thousandth of a gram.

The wear cylinder 14 is machined to a cylindrical shape. After further surface conditioning, the surface is lightly sand blasted, machined, etched, plated, etc., so as to yield a rough surface finish.

A sand blasted surface 60 is necessary to cause a measurable amount of specimen wear in a short time. By lightly sand blasting the wear cylinder surface 60, a roughness is created that tends to draw abrasive particles into the interface between the O-ring and the wear cylinder surface 60. This action causes three body abrasive wear to take place.

A test fluid 44 is prepared using water, sand and thickening agents. The resulting mixture holds the sand particles in suspension throughout the test. The sand consists of used sand-blast sand sifted to obtain minus one hundred mesh fine sand and dust.

Prior to testing, a new prepared test specimen 22 is mounted in each of the two specimen holders 20. The specimen holder assemblies 20 are then bolted to the bottom of the loading arms 16 by means of bolts 50. A new wear cylinder 14 is mounted in the chuck 10 by means of mounting shaft 12. Dead weights 24, corresponding to the proper specimen load, are connected to the loading arm cables 26. A container 42 with a 3" depth of test fluid 44 is raised through the hole in table top 30 to submerge the test specimens 22 and wear cylinder 14. A cover plate is placed over the hole to support the container 42 of test fluid 44.

The wear test machine is turned on and the wear cylinder is rotated at the desired speed for the specified test period. At the end of the test, the machine is shut off. The specimen holders 20, test specimens 22, bolts 50, and loading arms 16 are rinsed in cold water to remove the test fluid 44. After cleaning, the specimens 22 are weighed again on the analytical balance. The weight loss is then computed and recorded.

Thermocouples are used to record specimen temperatue. The specimens 22 are mounted in the specimen holder assembly 20 with the holes 56 for the thermocouples 48 on the top side of the O-ring segments 22. After the specimen holder assemblies 20 are bolted to the loading arms 16, the thermocouples 48 are gently inserted. The syringe type thermocouples 48 are easily bent and great care must be taken not to damage them. Specimen temperatures are monitored and recorded during the wear tests.

As will be apparent to those skilled in the art, many modifications may be made to the invention without departing from the spirit and scope thereof. Accordingly the invention is not limited to the exact form and arrangement in the embodiment disclosed. A foregoing description has made reference to a standard drill press chuck on the inventive device and to the shaft hangers which hold the loading arms. It should be appreciated that these terms are used for the sake of convenience and are not intended to limit the flexibility of the present invention. The chuck need not be from a drill press, but could be any coupling. The shaft holders could be any means of support for the load arms. The inventive device serves to test or measure wear of O-rings and dynamic coefficient properties between two surfaces in contact with one another.

Above a specific embodiment of the present invention has been described. It should be appreciated, however that this embodiment was described for purposes of illustration only, without any intention of limiting the scope of the present invention. Rather it is the intention that the present invention be limited not by the above but only as is defined in the appended claims.

What is claimed is:

1. An apparatus for measuring and testing O-ring wear and dynamic coefficient of friction characteristics of an O-ring surface and the like, the apparatus comprising; coupling means to hold and selectively rotate a wear cylinder during the wear test; at least one vertical loading arm mounted to pivot on support means in said apparatus; a specimen holding assembly at the bottom of the loading arm which holds at least one segment of the O-ring; a dead weight connected to the top of the loading arm by means of a steel cable on pully means for maintaining the wear specimen against the wear cylinder; a container of abrasive test fluid for immerson of the test specimens and wear cylinder; strain gauges mounted on the vertical loading arm which serve as a means for determining the friction force on the O-ring specimens; at least one thermocouple in the O-ring specimens for monitoring the temperature there of during the tests; a rough surface on the wear cylinder which tends to draw said abrasive test fluid into the interface between the wear cylinder and the O-ring segment causing wear involving the cylinder, the O-ring segment and the test fluid.

2. The apparatus recited in claim 1 wherein said wear cylinder has a surface finish to produce wear involving only the cylinder and the O-ring specimen.

3. The apparatus recited in claim 1 wherein said test fluid is a heated fluid.

4. The apparatus recited in claim 1 wherein a plurality of the loading arms are spaced around the wear cylinder.

5. The apparatus recited in claim 1 wherein, said wear cylinder surface is finished by means other than sand blasting; such as machining, grinding, chemical etching, plating, and so forth.

6. The apparatus recited in claim 1 wherein, said O-ring specimen is replaced with circular wire or tubing.

7. The apparatus recited in claim 1 wherein the wear cylinder rotation is reversed, or its rotational direction and speed can be controlled and any combination of speeds, displacements, and accelerations can be selectively obtained by said coupling means.

8. The apparatus recited in claim 1 wherein the wear cylinder and its mounting shaft can be raised or lowered vertically, by said coupling means continuously with the test, to produce a new wear surface as the test progresses or to expose the O-ring specimen to a vertical friction force.

* * * * *